United States Patent [19]

Derian et al.

[11] Patent Number: 5,409,885
[45] Date of Patent: Apr. 25, 1995

[54] HOMOGENEOUS, STABLE AND FLOWABLE AQUEOUS MIXTURES AND DISPERSIONS OF WATER-INSOLUBLE SUBSTANCES FORMULATED THEREFROM EXHIBITING OPTICAL BIREFRINGENCE

[75] Inventors: Paul-Joel Derian, Fontenay-Aux-Roses; Gilles Guerin, Eaubonne; Philippe Jost, Paris, all of France

[73] Assignee: Rhone-Poulenc Chimie, Courbevoie Cedex, France

[21] Appl. No.: 911,092

[22] Filed: Jul. 9, 1992

[30] Foreign Application Priority Data

Jul. 9, 1991 [FR] France ................. 91 09005

[51] Int. Cl.[6] ................. A01N 25/30; A01N 43/40; A01N 39/04
[52] U.S. Cl. ................. 504/116; 504/257; 504/323; 71/DIG. 1; 514/143; 514/385; 514/417; 514/471; 514/521; 514/755; 514/937
[58] Field of Search ................. 504/323, 116, 257; 514/937; 71/DIG. 1

[56] References Cited

U.S. PATENT DOCUMENTS

| | | | |
|---|---|---|---|
| 3,764,293 | 10/1973 | Guth | 71/117 |
| 4,431,834 | 2/1984 | Cartwright | 504/323 |
| 4,626,274 | 12/1986 | Hausmann et al. | 71/DIG. 1 |
| 4,813,399 | 3/1989 | Schapira et al. | 71/DIG. 1 |
| 4,975,113 | 12/1990 | Marrs et al. | 71/DIG. 1 |
| 4,995,900 | 2/1991 | Futcher | 71/DIG. 1 |

FOREIGN PATENT DOCUMENTS

| | | |
|---|---|---|
| 987925 | 4/1976 | Canada . |
| 0388239 | 9/1990 | European Pat. Off. . |
| 1397568 | 5/1965 | France . |
| 1408238 | 7/1965 | France . |

*Primary Examiner*—Peter O'Sullivan
*Assistant Examiner*—S. Mark Clardy
*Attorney, Agent, or Firm*—Burns, Doane, Swecker & Mathis

[57] ABSTRACT

Stable and flowable aqueous dispersions of at least one water-insoluble material are formulated by dispersing such water-insoluble material, e.g., solid particulates of a plant protection compound, into a homogeneous, stable and flowable aqueous composition that includes (1) at least one water-soluble derivative of a plant protection active agent bearing at least one ionizable functional group and at least one hydrophilic functional group, (2) at least one nonionic surface-active agent and/or at least one aliphatic, cycloaliphatic or arylaliphatic alcohol having from 4 to 15 carbon atoms, and (3) water, this composition exhibiting optical birefringence and a yield point of at least 0.1 pascal.

21 Claims, No Drawings

HOMOGENEOUS, STABLE AND FLOWABLE AQUEOUS MIXTURES AND DISPERSIONS OF WATER-INSOLUBLE SUBSTANCES FORMULATED THEREFROM EXHIBITING OPTICAL BIREFRINGENCE

BACKGROUND OF THE INVENTION

1. Field of the Invention

The present invention relates to homogeneous stable and flowable aqueous mixtures which can be formulated, with water-insoluble substances, into stable and flowable dispersions, notably for plant/crop protection.

2. Description of the Prior Art

It is known to this art that, when it is desired to maintain water-insoluble substances in dispersion in water, it is necessary to prepare relatively complex formulations which contain, especially, in addition to the water and the insoluble substance, a plurality of surface-active agents and a thickener.

SUMMARY OF THE INVENTION

A major object of the present invention is the provision of homogeneous, stable and flowable aqueous mixtures comprising (1) at least one water-soluble derivative of a plant protection active agent, said derivative containing at least one ionizable functional group and at least one hydrophobic functional group, (2) at least one nonionic surface-active agent and/or at least one aliphatic, cycloaliphatic or arylaliphatic alcohol having from 4 to 15 carbon atoms, and (3) water, with the proviso that such aqueous mixtures exhibit a yield point equal to or greater than 0.1 pascal.

DETAILED DESCRIPTION OF THE PREFERRED EMBODIMENTS OF THE INVENTION

More particularly according to the present invention, the plant protection active agents of which the water-soluble derivatives are used for the formulation of the subject mixtures are very many and varied and are too numerous to mention.

Exemplary ionizable functional groups comprising the above soluble derivatives are the carboxylic acid salt groups, the other acid salts, the ammonium or the phosphonium functional groups, etc.

Among the water-soluble derivatives of the plant protection active agents, various categories thereof are particularly representative.

Suitable such derivatives therefore include the water-soluble derivatives, obtained by at least partial neutralization of the acid functions, for example by means of alkali metal hydroxides such as potassium hydroxide or sodium hydroxide, by ammonia, by amines and, more particularly, alkanolamines such as monoethanolamine, diethanolamine or triethanolamine, of the plant protection active agents having the general formula (I):

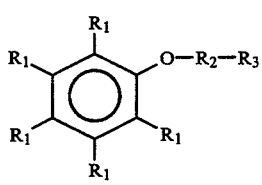

in which the radicals $R_1$, which may be identical or different, are each a hydrogen atom, a chlorine atom or a methyl radical; $R_2$ is a linear or branched chain alkylene radical having from 1 to 4 carbon atoms such as ethylidene, methylene, ethylene, trimethylene or tetramethylene; and $R_3$ is —COOH or —O—SO$_3$H.

Exemplary commercially available compounds of the formula (I) include:

Mecoprop [(RS)-2-(4-chloro-ortho-tolyloxy)propionic acid],
2,4-D [2,4-dichlorophenoxyacetic acid],
2,4-DB [4-(2,4-dichlorophenoxy)butyric acid],
2,4-DES [2-(2,4-dichlorophenoxy)ethyl hydrogen sulfate],
Dichlorprop [2-(2,4-dichlorophenoxy)propionic acid],
Fenoprop [2-(2,4,5-trichlorophenoxy)propionic acid],
MCPA [4-chloro-ortho-tolyloxyacetic acid],
MCPB [4-(4-chloro-ortho-tolyloxy)butyric acid],
2,4,5-T (2,4,5-trichlorophenoxyacetic acid).

Also very suitable are the water-soluble derivatives, obtained by the at least partial neutralization of the acid functions, for example by alkali metal hydroxides such as potassium hydroxide or sodium hydroxide, by ammonia, by amines and, more particularly, by alkanolamines such as monoethanolamine, diethanolamine or triethanolamine, of the plant protection active agents having the general formula (II):

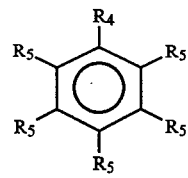

in which $R_4$ is —COOH or —CH$_2$—COOH; and the radicals $R_5$, which may be identical or different, are each a hydrogen atom, a chlorine atom, an —NH$_2$ group or a methoxy radical.

Exemplary commercially available compounds of the formula (II) include:

Chloramben [3-amino-2,5-dichlorobenzoic acid],
Dicamba [3,6-dichloro-ortho-anisic acid],
Chlorfenac [2,3,6-trichlorophenylacetic acid],
2,3,6-TBA [2,3,6-trichlorobenzoic acid].

Also suitable for the mixtures of the invention are the water-soluble derivatives, obtained by the at least partial neutralization of the acid functions, for example by alkali metal hydroxides such as potassium hydroxide or sodium hydroxide, by ammonia, by amines and, more particularly, by alkanolamines such as monoethanolamine, diethanolamine or triethanolamine, of the plant protection active agents having the general formula (III):

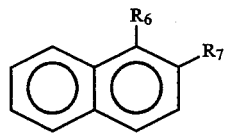

in which the radicals $R_6$ and $R_7$, which may be identical or different, are each a hydrogen atom, a —COOH group, a —CH$_2$—COOH group or a —O—CH$_2$—COOH group.

Exemplary commercially available compounds of formula (III) include:
(1-Naphthyl)acetic acid,
(2-Naphthyloxy)acetic acid.

Also suitable for the mixtures of the invention are the water-soluble derivatives, obtained by the at least partial neutralization of the acid functions, for example by alkali metal hydroxides, by ammonia or by the amines as indicated above, of the plant protection active agents having the general formula (IV):

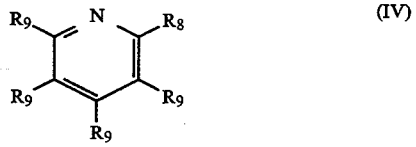

in which $R_8$ is a —COOH group or a —O—CH$_2$—COOH group; and the radicals 9, which may be identical or different, are each a hydrogen atom, a chlorine atom or a —NH$_2$ group.

Exemplary commercially available compounds of formula (IV) include:
Picloram (4-amino-3,5,6-trichloropicolinic acid),
Triclopyr (3,5,6-trichloro-2-pyridinyloxyacetic acid).

Other water-soluble derivatives of plant protection active agents not corresponding to the above general formulae (I) and (IV) can also be used; the soluble derivatives can either be the active agents themselves, or the products obtained by the at least partial neutralization of the optional acid functions. Such plant protection active agents include, for example:
Benazolin [(4-chloro-2,3-dihydro-2-oxo-1,1,3-benzothiazol-3-yl)acetic acid],
Benomyl [methyl 1-(butylcarbamoyl)-2-benzimidazolecarbamate],
Chlormequat (2-chloroethyltrimethylammonium),
Chloroacetic acid,
Chlorphonium [tributyl(2,4-dichlorobenzyl)phosphonium],
Dalapon [2,2-dichloropropionic acid],
Daminozide [N-dimethylaminosuccinamic acid],
Endothal [7-oxabicyclo[2.2.1]heptane-2,3-dicarboxylic acid],
Fosetyl [ethyl hydroen phosphonate],
Paraquat [1,1'-dimethyl-4,4'-bipyridinium],
Quizalofop [(RS)-2-[4-(6-chloroquinoxalin-2-yloxy)-phenoxy]propionic acid],
Sodium fluoroacetate.

A plurality of water-soluble derivatives of the plant protection active agents can be formulated into the mixtures of the invention.

Exemplary nonionic surface-active agents which can be formulated into the homogeneous, stable and flowable aqueous mixtures of the invention include:
The ethoxylated or ethoxypropoxylated fatty alcohols,
The ethoxylated or ethoxypropoxylated triglycerides,
The ethoxylated or ethoxypropoxylated fatty acids,
The ethoxylated or ethoxypropoxylated sorbitan esters,
The ethoxylated or ethoxypropoxylated fatty amines,
The ethoxylated or ethoxypropoxylated di(1-phenylethyl)phenols,
The ethoxylated or ethoxypropoxylated tri(1-phenylethyl)phenols,
The ethoxylated or ethoxypropoxylated alkylphenols.

The number of ethylene oxide (EO) and/or propylene oxide (PO) units comprising these nonionic surface-active agents typically ranges from 2 to 100 according to the desired HLB (hydrophilism/lipophilism balance).

Preferably, the number of EO and/or PO units ranges from 2 to 50.

The ethoxylated or ethoxypropoxylated fatty alcohols advantageously have from 6 to 22 carbon atoms, the EO and PO units being excluded from these numbers, and are preferably ethoxylated.

The ethoxylated or ethoxypropoxylated triglycerides are advantageously triglycerides of vegetable or animal origin (such as lard, tallow, groundnut oil, butter oil, cottonseed oil, linseed oil, olive oil, palm oil, grapeseed oil, fish oil, soya bean oil, castor oil, rapeseed oil, copra oil or coconut oil) and are preferably ethoxylated.

The ethoxylated or ethoxypropoxylated fatty acids are esters of fatty acids (such as, for example, oleic acid or stearic acid), and are preferably ethoxylated.

The ethoxylated or ethoxypropoxylated esters of sorbitan are advantageously esters of cyclized sorbitol with $C_{10}$ to $C_{20}$ fatty acids such as lauric acid, stearic acid or oleic acid, and are preferably ethoxylated.

By the term "ethoxylated triglyceride" are intended both the products obtained by ethoxylation of a triglyceride by ethylene oxide and those obtained by transesterification of a triglyceride by a polyethylene glycol.

Likewise, by the term "ethoxylated fatty acid" are intended both the products obtained by ethoxylation of a fatty acid by ethylene oxide and those obtained by esterification of a fatty acid by a polyethylene glycol.

The ethoxylated or ethoxypropoxylated fatty amines generally have from 10 to 22 carbon atoms, the EO and PO units being excluded from these numbers, and are preferably ethoxylated.

The ethoxylated or ethoxypropoxylated alkylphenols advantageously have 1 or 2, linear or branched, alkyl groups having from 4 to 12 carbon atoms, particularly octyls, nonyls or dodecycls.

Exemplary of the nonionic surface-active agents of the ethoxylated or ethoxypropoxylated alkylphenols, the ethoxylated di(1-phenylethyl)phenols and the ethoxylated or ethoxypropoxylated tri(1-phenylethyl)-phenols, the following are representative:
Di(1-phenylethyl)phenol ethoxylated by 5 EO units,
Di(1-phenylethyl)phenol ethoxylated by 10 EO units,
Tri(1-phenylethyl)phenol ethoxylated by 16 EO units,
Tri(1-phenylethyl)phenol ethoxylated by 20 EO units,
Tri(1-phenylethyl)phenol ethoxylated by 25 EO units,
Tri(1-phenylethyl)phenol ethoxylated by 40 EO units,
Tri(1-phenylethyl)phenols ethoxypropoxylated by 25 EO+PO units,
Nonylphenol ethoxylated by 2 EO units,
Nonylphenol ethoxylated by 4 EO units,
Nonylphenol ethoxylated by 6 EO units,
Nonylphenol ethoxylated by 9 EO units,
Nonylphenols ethoxypropoxylated by 25 EO+PO units,
Nonylphenols ethoxypropoxylated by 30 EO+PO units, Nonylphenols ethoxypropoxylated by 40 EO+PO units, Nonylphenols ethoxypropoxylated by 55 EO+PO units, Nonylphenols ethoxypropoxylated by 80 EO+PO units.

The alcohols which can be formulated into the homogeneous, stable and flowable aqueous mixtures of the invention, together with or in lieu of the nonionic surface-active agents, are preferably linear- or branched-chain aliphatic alcohols or cycloaliphatic alcohols having from 10 to 15 carbon atoms.

Exemplary of such alcohols are n-decanol, n-dodecanol, n-undecanol, n-tridecanol, n-tetradecanol or n-pentadecanol and their respective branched, primary, secondary or tertiary isomers.

Of course, a plurality of nonionic surface-active agents, a plurality of alcohols, or mixtures of nonionic surface-active agents and alcohols can be used.

The homogeneous stable and flowable aqueous mixtures of the invention typically contain, overall, from 1% to 70% by weight, relative to their total weight, of water-soluble derivative of plant protection active agents, of nonionic surface-active agent and/or of alcohol, the remainder being water.

Preferably, the yield point of these mixtures is equal to or higher than 0.2 pascal.

The weight ratio soluble derivative of plant protection active agent/nonionic surface-active agent and/or alcohol advantageously ranges from 80/20 to 10/90 and preferably from 70/30 to 20/80.

The water used in these mixtures can be pure water or aqueous salt solutions such as, for example, sodium chloride.

The homogeneous, stable and flowable aqueous mixtures of the invention are typically formulated by dissolving the soluble derivative(s) of the plant protection active material in water.

The nonionic surface-active agent and/or the alcohol are then progressively added until an optical birefringence is obtained (characteristic of a nonisotropic mesomorphic phase), such as can be seen in the crossed polarizer of an optical microscope.

These homogeneous, stable and flowable aqueous mixtures which exhibit optical birefringence have viscoelastic properties such that they permit the formation of stable dispersions of water-insoluble substances.

This invention also features the use of the homogeneous, stable and flowable aqueous mixtures for the preparation of stable aqueous dispersions of water-insoluble substances, which are typically solid, water-insoluble, plant protection active agents.

By "water-insoluble substance or active agent" are intended substances or active agents whose solubility in water at 20° C. is less than 5 grams/liter.

These plant protection active agents can be, for example, insecticides, germicides, herbicides, fungicides, acaricides, nematocides, molluscicides, rodenticides, attractants, repellents or combinations thereof.

Exemplary active agents which are suitable for formulation into the stable dispersions of the invention include:
 Diflufenican,
 Deltamethrin,
 Propham,
 Tetramethrin,
 Furalaxyl,
 Heptachlor,
 Propanil,
 Oxadiazon,
 Triflumizole,
 Dimethametryn,
 Atrazine,
 Diuron,
 Neburon,
 Linuron,
 Isoproturon,
 Simazine,
 Ametryn,
 Phenmedipham,
 Pendimethalin.

In the dispersions of insoluble active agent in the homogeneous, flowable aqueous mixtures, the amount of insoluble active agent in dispersion does not generally exceed 60% by weight per total volume of dispersion, in order to preserve the "flowable" character of such dispersion.

The low-limit is obviously not critical and, depending upon the intended final application, it is possible to provide concentrations of insoluble active agent as low as 0.1% by weight per total volume of dispersion.

The viscoelastic properties of the homogeneous, stable and flowable aqueous mixtures used to disperse water-insoluble active agents allow avoiding having to incorporate thickening agents such as polysaccharides, for example xanthan gum, which are typically present in dispersions of this type.

The dispersions of the invention can, on the other hand, contain the usual adjuvants for this type of formulation, such as antifoaming agents, for example the polyorganosiloxanes, an antifreeze, such as monopropylene glycol or monoethylene glycol, or preservatives.

The dispersions of insoluble plant protection active agents prepared from the homogeneous, stable and flowable aqueous mixtures are themselves stable within a temperature range of from $-5°$ C. to $+45°$ C. for several months.

They do not display any flocculation, crystallization or sedimentation phenomena on storage.

They can also be used as such or after dilution with water at the point in time of their intended application.

In order to further illustrate the present invention and the advantages thereof, the following specific examples are given, it being understood that same are intended only as illustrative and in nowise limitative.

In said examples to follow, the yield point was measured, which is representative of the shear stress which is necessary to exert on the fluid to make it flow, as well as, in certain cases, the pseudoplasticity index, which is a good indication of the flowability of the solution. These two properties were estimated by rheological measurements using a Rheomat 30 viscometer equipped with a coaxial measurement system reference A. The yield point was calculated from the measurements via the Bingham model.

EXAMPLE 1

8.11 g of 4-chloro-ortho-tolyloxyacetic acid (MCPA) were dissolved at room temperature in 80.27 g of an aqueous solution (containing 10 g/liter of sodium chloride) and 1.62 g of NaOH, to convert the MCPA into its sodium salt.

A linear-chain alcohol containing 10 to 12 carbon atoms (commercially available under the trademark Alfol) was added to this solution until an optical birefringence (observed in an optical microscope) was obtained.

This optical birefringenced was obtained by the addition of 10 g of the $C_{10}$–$C_{12}$ alcohol.

The resulting mixture was a clear and colorless solution having a yield point higher than 0.2 Pa.

It remained stable for more than 6 months at temperature cycles of −5° C., +45° C.

EXAMPLES 2 TO 8

The procedure of Example 1 was repeated and homogeneous, stable and flowable aqueous mixtures were prepared having the compositions reported in Table 1 below.

All of these mixtures were clear and colorless solutions which remained stable for more than 6 months at temperature cycles of −5° C., +45° C.

TABLE 1

| Examples | Soluble derivative of plant protection active agent | | Alcohol or nonionic surface-active agent | $H_2O$ (concentration of NaCl) | Yield point |
|---|---|---|---|---|---|
| Example 2 | MCPA | 11.72 g | Alfol: 35.0 g | 50.94 g (10 g/l) | >0.2 Pa |
|  | NaOH | 2.34 g | *** | | |
| Example 3 | MCPA | 8.11 g | Soprophor BC2: 12.0 g | 78.25 g (10 g/l) | >0.2 Pa |
|  | NaOH | 1.62 g | *** | | |
| Example 4 | MCPA | 13.02 g | Soprophor BC2: 30.0 g | 54.32 g (10 g/l) | >0.2 Pa |
|  | NAOH | 2.61 g | | | |
| Example 5 | 2,4-D* | 8.11 g | Alfol: 8.0 g | 81.84 g (12.5 g/l) | >0.2 Pa |
|  | KOH | 2.05 g | | | |
| Example 6 | 2,4-D* | 14.07 g | Alfol: 18.0 g | 64.36 g (12.5 g/l) | >0.2 Pa |
|  | KOH | 3.57 g | | | |
| Example 7 | Mecoprop** | 17.0 g | Alfol: 26.0 g | 52.57 g (20 g/l) | >0.2 Pa |
|  | KOH | 4.43 g | | | |
| Example 8 | Mecoprop** | 25.49 g | Alfol: 34.0 g | 33.86 g (20 g/l) | >0.2 Pa |
|  | KOH | 6.65 g | | | |

*2,4-D = 2,4-dichlorophenoxyacetic acid
**Mecoprop = (RS)-2-(4-chloro-ortho-tolyloxy)propionic acid
***Soprophor BC2 = ethoxylated nonylphenol containing an average of 2 EO units

EXAMPLES 9 TO 12

The procedure of Example 1 was repeated and homogeneous, stable and flowable aqueous mixtures were prepared having the compositions reported in Table 2 below.

All of the mixtures obtained were clear and colorless solutions, which remained stable for more ethan 6 months at temperature cycles of −5° C., +45° C.

In addition to the yield point of these mixtures, the following were also measured:

(a) The pseudoviscosity index $$n = 1 + \frac{\log(\eta_1) - \log(\eta_2)}{\log(\gamma_1) - \log(\gamma_2)}$$

$\eta$ = viscosity (Pa.s) at a velocity gradient ($\gamma_1$) of 1 $s^{-1}$ $\gamma$ = viscosity (Pa.s) at a velocity gradient ($\gamma_2$) of 10 $s^{-1}$ (b) the viscosity in Pa.s (at a velocity gradient of 10 $s^{-1}$)

TABLE 2

| Examples | Soluble derivative of plant protection active agent | | Alcohol or nonionic surface-active agent | $H_2O$ (with 10 g/l NaCl) | Yield point | Pseudo-plasticity index | Viscosity (in Pa s) |
|---|---|---|---|---|---|---|---|
| Example 9 | 2,4-D | 13.65 g | Alfol: 20.0 g | 62.89 g | 1.67 | 0.65 | 2.7 |
|  | KOH | 3.46 g | | | | | |
| Example 10 | 2,4-D | 8.09 g | Alfol: 5.0 g | 84.96 g | 0.48 | 0.49 | 0.80 |
|  | KOH | 2.05 g | | | | | |
| Example 11 | MCPA | 8.11 g | Soprophor BC2: 13.0 g | 77.26 g | 1.51 | 0.39 | 0.59 |
|  | NaOH | 1.62 g | | | | | |
| Example 12 | MCPA | 12.17 g | Soprophor BC2: 33.0 g | 52.41 g | 3.75 | 0.41 | 0.71 |
|  | NaOH | 2.43 g | | | | | |

EXAMPLE 13

The procedure of Example 1 was repeated and a homogeneous, stable and flowable aqueous mixture having the following composition was prepared:

(i) Mecoprop neutralized by KOH: 15 g
(ii) Alfol: 12 g
(iii) H20 (at 20 g/l of NaCl): 73 g Into this clear and colorless mixture was dispersed 1 g of diflufenican, which is a water-insoluble herbicide (solubility at 20° C. of $5 \times 10^{-5}$ g/l).

The dispersion was stable for more than 6 months in a temperature cycle of −5° C., +45° C.

EXAMPLE 14

The procedure of Example 1 was repeated and a homogeneous, stable and flowable aqueous mixture having the following composition was prepared:

(i) Mecoprop neutralized by KOH: 35 g
(ii) Alfol: 28 g
(iii) H20 (at 20 g/l of NaCl): 37 g Into this clear and colorless mixture was dispersed 1 g of diflufenican, which is a water-insoluble herbicide (solubility at 20° C. of $5 \times 10^{-5}$ g/l).

The dispersion was stable for more than 6 months in a temperature cycle of −5° C., +45° C.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A homogeneous, stable and flowable aqueous composition, comprising (1) at least one water-soluble derivative of a plant protection active agent bearing at least one ionizable functional group and at least one hydrophobic functional group, (2) at least one nonionic surface-active agent and/or at least one aliphatic cycloaliphatic or arylaliphatic alcohol having from 4 to 15 carbon atoms, and (3) water, said composition exhibiting a yield point of at least 0.1 pascal, wherein said at least one nonionic surface-active agent and/or at least one aliphatic cycloaliphatic or arylaliphatic alcohol having from 4 to 15 carbon atoms is present in an amount sufficient to obtain an optical birefringence.

2. A process for the preparation of the aqueous composition as defined by claim 1, comprising (a) dissolving said at least one water-soluble derivative (1) in water, and (b) progressively adding said at least one nonionic surface-active agent and/or at least one alcohol (2) to the resulting solution until optical birefringence is attained.

3. The aqueous composition as defined by claim 1, devoid of any thickening agent.

4. The aqueous composition as defined by claim 1, said at least one water-soluble derivative (1) comprising an at least partially neutralized plant protection active agent having the formula (I):

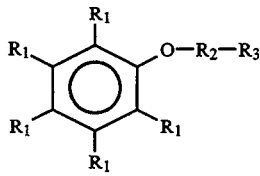

in which the radicals $R_1$, which may be identical or different, are each a hydrogen atom, a chlorine atom or a methyl radical; $R_2$ is a linear or branched chain alkylene radical having from 1 to 4 carbon atoms; and $R_3$ is —COOH or —O—SO$_3$H.

5. The aqueous composition as defined by claim 1, said at least one water-soluble derivative (1) comprising an at least partially neutralized plant protection active agent having the formula (II):

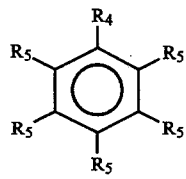

in which $R_4$ is —COOH or —CH$_2$—COOH; and the radicals $R_5$, which may be identical or different, are each a hydrogen atom, a chlorine atom, an —NH$_2$ group or a methoxy radical.

6. The aqueous composition as defined by claim 1, said at least one water-soluble derivative (1) comprising an at least partially neutralized plant protection active agent having the formula (III):

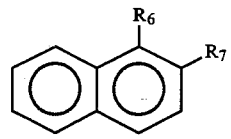

in which the radicals $R_6$ and $R_7$, which may be identical or different, are each a hydrogen atom, a —COOH group, a —CH$_2$—COOH group or a —O—CH$_2$—COOH group.

7. The aqueous composition as defined by claim 1, said at least one water-soluble derivative (1) comprising an at least partially neutralized plant protection active agent having the formula (IV):

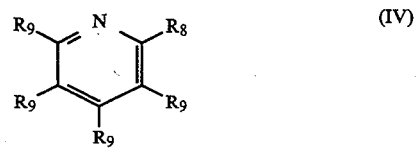

in which $R_8$ is a —COOH group or a —O—CH$_2$—COOH group; and the radicals $R_9$, which may be identical or different, are each a hydrogen atom, a chlorine atom or a —NH$_2$ group.

8. The aqueous composition as defined by claim 1, said at least one water-soluble derivative (1) comprising an at least partially neutralized plant protection active agent selected from among (RS)-2-(4-chloro-ortho-tolyloxy)propionic acid; 2,4-dichlorophenoxyacetic acid; 4-(2,4-dichlorophenoxy)butyric acid; 2-(2,4-dichlorophenoxy)ethyl hydrogen sulfate; 2-(2,4-dichlorophenoxy)propionic acid; 2-(2,4,5-trichlorophenoxy)propionic acid; 4-chloro-ortho-tolyloxyacetic acid; 4-(4-chloro-ortho-tolyloxy)butyric acid; 2,4,5-trichlorophenoxyacetic acid; 3-amino-2,5-dichlorobenzoic acid; 3,6-dichloro-ortho-anisic acid; 2,3,6-trichlorophenylacetic acid; 2,3,6-trichlorobenzoic acid; (1-naphthyl)acetic acid; (2-naphthyloxy)acetic acid; 4-amino-3,5,6-trichloropicolinic acid; 3,5,6-trichloro-2-pyridinyloxyacetic acid; (4-chloro-2,3-dihydro-2-oxo-1,3-benzothiazol-3-yl)acetic acid; methyl 1-(butylcarbamoyl)-2-benzimidazolecarbamate; 2-chloroethyltrimethylammonium; chloroacetic acid; tributyl(2,4-dichloroenzyl)phosphonium; 2,2-dichloropropionic acid; N-dimethylaminosuccinamic acid; 7-oxabicyclo[2.2.1]heptane-2,3-dicarboxylic acid; ethyl hydrogen phosphonate; 1,1'-dimethyl-4,4'-bipyridinium; (RS)-2-[4-(6-chloroquinoxalin-2-yloxy)phenoxy]propionic acid; and sodium fluoroacetate.

9. The aqueous composition as defined by any of claims 4, 5, 6, 7 or 8, said at least one water-soluble derivative (1) having had the acid functions thereof at least partially neutralized by an alkali metal hydroxide, ammonia, an amine or an alkanolamine.

10. The aqueous composition as defined by claim 1, comprising at least one nonionic surface-active agent (2) selected from among an ethoxylated or ethoxypropoxylated fatty alcohol; an ethoxylated or ethoxypropoxylated triglyceride; an ethoxylated or ethoxypropoxylated fatty acid; an ethoxylated or ethoxypropoxylated sorbitan ester; an ethoxylated or ethoxypropoxylated fatty amine; an ethoxylated or ethoxypropoxylated di(1-phenylethyl)phenol; an ethoxylated or ethoxypropoxylated tri(1-phenylethyl)phenol; and an ethoxylated or ethoxypropoxylated alkylphenol.

11. The aqueous composition as defined by claim 1, comprising at least one aliphatic or cycloaliphatic alcohol (2).

12. The aqueous composition as defined by claim 1, exhibiting a yield point of at least 0.2 pascal.

13. The aqueous composition as defined by claim 1, wherein the weight ratio water-soluble derivative (1)/nonionic surface-active agent and/or alcohol (2) ranges from 80/20 to 10/90.

14. The aqueous composition as defined by claim 13, said ratio ranging from 70/30 to 20/80.

15. The aqueous composition as defined by claim 1, comprising from 1% to 70% by total weight thereof, of said at least one water-soluble derivative (1) and said at least one nonionic surface-active agent and/or alcohol (2).

16. A homogeneous, stable and flowable aqueous composition, comprising (1) at least one water-insoluble plant protection active agent, (2) at least one nonionic surface-active agent and/or at least one aliphatic cycloaliphatic or arylaliphatic alcohol having from 4 to 15 carbon atoms, and (3) water, said composition exhibiting a yield point of at least 0.1 pascal and an optical birefringence.

17. A stable aqueous dispersion comprising at least one water-insoluble material dispersed in the homogeneous aqueous composition as defined by claim 1.

18. The stable aqueous dispersion as defined by claim 17, said at least one water-insoluble material comprising solid particulates of at least one plant protection active agent.

19. The stable aqueous dispersion as defined by claim 18, said at least one plant protection active agent comprising an insecticide, germicide, herbicide, fungicide, acaricide, nematocide, molluscicide, rodenticide, attractant, repellent, or combinations thereof.

20. The stable aqueous dispersion as defined by claim 18, said at least one plant protection active agent comprising diflufenican, deltamethrin, propham, tetramethrin, furalaxyl, heptachlor, propanil, oxadiazon, triflumizole, dimethametryn, atrazine, diuron, neburon, linuron, isoproturon, simazine, ametryn, phenmedipham, or pendimetehalin.

21. The stable aqueous dispersion as defined by claim 17, comprising up to 60% by weight of said at least one water-insoluble material per total volume thereof.

* * * * *